(12) United States Patent
Ashland

(10) Patent No.: US 9,468,435 B2
(45) Date of Patent: Oct. 18, 2016

(54) WOUND CLOSURE DEVICE

(75) Inventor: Ian Ashland, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 954 days.

(21) Appl. No.: 12/646,188

(22) Filed: Dec. 23, 2009

(65) Prior Publication Data

US 2011/0152889 A1 Jun. 23, 2011

(51) Int. Cl.
*A61B 17/04* (2006.01)

(52) U.S. Cl.
CPC ................ *A61B 17/0487* (2013.01)

(58) Field of Classification Search
CPC ............ A61B 17/0487; A61B 17/04; A61M 2025/09125
USPC ....... 606/215, 144, 148, 139, 232; 24/115 G
See application file for complete search history.

(56) References Cited

U.S. PATENT DOCUMENTS

| 4,288,891 | A | * | 9/1981 | Boden ................ F16G 11/10 |
| | | | | 24/115 G |
| 4,291,698 | A | | 9/1981 | Fuchs et al. |
| 4,453,292 | A | * | 6/1984 | Bakker ................ F16G 11/10 |
| | | | | 24/115 G |
| D301,373 | S | | 5/1989 | Peters |
| 5,021,059 | A | | 6/1991 | Kensey et al. |
| 5,059,201 | A | | 10/1991 | Asnis |
| 5,089,012 | A | | 2/1992 | Prou |
| 5,160,339 | A | | 11/1992 | Chen et al. |
| 5,171,253 | A | | 12/1992 | Klieman |
| 5,324,306 | A | | 6/1994 | Makower et al. |

(Continued)

FOREIGN PATENT DOCUMENTS

| WO | WO 2006/050080 A2 | 5/2006 |
| WO | WO 2008/033766 A2 | 3/2008 |

(Continued)

OTHER PUBLICATIONS

"A Modified Lateral Technique for the Insertion of Peritoneal Dialysis Catheters Enabling Immediate Start of Dialysis." *Peritoneal Dialysis International*, vol. 18, pp. 329-341; 1998 International *Society* for Peritoneal Dialysis.

(Continued)

*Primary Examiner* — Gregory Anderson
*Assistant Examiner* — Christina Lauer
(74) *Attorney, Agent, or Firm* — Brinks Gilson & Lione

(57) ABSTRACT

A wound closure device for promoting hemostasis includes a polyhedral body comprising a proximal body end portion and a distal body end portion, including a suture channel horizontally extending through the proximal and distal body end portions, the suture channel containing proximal and distal suture channel openings. An actuator system includes a suture engagement member configured to selectively facilitate axial movement or release of one or more sutures through the channel in an open configuration, and to facilitate securement of suture(s) in the channel in a locked configuration. The proximal body end portion includes a face configured to contact a body surface, anchoring the body to the body surface when suture(s) are secured under tension by the engagement member in the locked position. Once the sutures are secured, the device lends itself to hands-free anchoring until hemostasis is achieved. The device and sutures may then be removed that same day, shortly thereafter.

8 Claims, 3 Drawing Sheets

(56) References Cited

U.S. PATENT DOCUMENTS

| | | | |
|---|---|---|---|
| 5,325,868 A * | 7/1994 | Kimmelstiel | 600/585 |
| 5,413,585 A | 5/1995 | Pagedas | |
| 5,507,775 A | 4/1996 | Ger et al. | |
| 5,514,159 A * | 5/1996 | Matula | A61B 17/0487 24/115 H |
| 5,735,877 A | 4/1998 | Pagedas | |
| 5,741,301 A | 4/1998 | Pagedas | |
| 5,778,904 A * | 7/1998 | Elsner | 132/275 |
| 5,817,072 A | 10/1998 | Lampropoulos et al. | |
| 5,820,596 A | 10/1998 | Rosen et al. | |
| 5,823,967 A | 10/1998 | McArthur | |
| 5,830,157 A | 11/1998 | Foote | |
| 5,911,728 A * | 6/1999 | Sepetka et al. | 606/151 |
| 5,921,968 A | 7/1999 | Lampropoulos et al. | |
| 5,951,517 A | 9/1999 | Lampropoulos et al. | |
| 5,957,865 A | 9/1999 | Backman et al. | |
| 5,957,901 A | 9/1999 | Mottola et al. | |
| 5,968,017 A | 10/1999 | Lampropoulos et al. | |
| 5,980,492 A | 11/1999 | Rosen et al. | |
| 5,984,895 A | 11/1999 | Padilla et al. | |
| 6,015,428 A | 1/2000 | Pagedas | |
| 6,050,981 A | 4/2000 | Lampropoulos et al. | |
| 6,053,935 A | 4/2000 | Brenneman et al. | |
| 6,059,758 A | 5/2000 | Padilla et al. | |
| 6,059,759 A | 5/2000 | Mottola et al. | |
| 6,066,160 A | 5/2000 | Colvin et al. | |
| 6,093,182 A | 7/2000 | Lampropoulos et al. | |
| 6,099,511 A | 8/2000 | Devos et al. | |
| 6,126,677 A | 10/2000 | Ganaja et al. | |
| 6,134,754 A | 10/2000 | Hansson et al. | |
| 6,139,523 A | 10/2000 | Taylor et al. | |
| D433,753 S | 11/2000 | Weiss | |
| 6,143,004 A | 11/2000 | Davis et al. | |
| 6,170,785 B1 | 1/2001 | Lampropoulos et al. | |
| 6,179,815 B1 | 1/2001 | Foote | |
| 6,179,816 B1 | 1/2001 | Mottola et al. | |
| 6,179,828 B1 | 1/2001 | Mottola et al. | |
| 6,200,329 B1 | 3/2001 | Fung et al. | |
| 6,214,332 B1 | 4/2001 | Askill et al. | |
| 6,264,676 B1 | 7/2001 | Gellman et al. | |
| 6,287,280 B1 | 9/2001 | Lampropoulos et al. | |
| 6,293,961 B2 | 9/2001 | Schwartz et al. | |
| 6,394,977 B1 | 5/2002 | Taylor et al. | |
| 6,402,723 B1 | 6/2002 | Lampropoulos et al. | |
| 6,471,715 B1 | 10/2002 | Weiss | |
| 6,508,789 B1 | 1/2003 | Sinnott et al. | |
| 6,533,757 B1 | 3/2003 | Lampropoulos et al. | |
| 6,537,266 B1 | 3/2003 | Mottola et al. | |
| 6,547,072 B2 | 4/2003 | Whiting et al. | |
| 6,572,590 B1 | 6/2003 | Stevens et al. | |
| 6,623,510 B2 | 9/2003 | Belef et al. | |
| 6,626,930 B1 | 9/2003 | Allen et al. | |
| 6,719,017 B1 | 4/2004 | McArthur et al. | |
| 6,800,069 B2 | 10/2004 | Lampropoulos et al. | |
| 6,814,427 B2 | 11/2004 | Taylor | |
| 6,860,895 B1 | 3/2005 | Akerfeldt et al. | |
| 6,939,357 B2 | 9/2005 | Navarro et al. | |
| 6,966,893 B2 | 11/2005 | Holtby et al. | |
| 7,033,379 B2 | 4/2006 | Peterson | |
| 7,035,741 B2 | 4/2006 | Taylor | |
| 7,087,060 B2 | 8/2006 | Clark | |
| 7,144,412 B2 | 12/2006 | Wolf et al. | |
| 7,182,750 B2 | 2/2007 | Lampropoulos et al. | |
| 7,204,841 B2 | 4/2007 | Green | |
| 7,261,703 B2 | 8/2007 | Lampropoulos et al. | |
| 7,351,249 B2 | 4/2008 | Hnojewyj et al. | |
| 7,407,505 B2 | 8/2008 | Sauer et al. | |
| 7,458,463 B2 | 12/2008 | Lampropoulos | |
| 7,468,068 B2 | 12/2008 | Kolster | |
| 7,470,256 B2 | 12/2008 | Lampropoulos et al. | |
| 7,520,869 B2 | 4/2009 | Lampropoulos et al. | |
| 7,530,970 B2 | 5/2009 | McArthur et al. | |
| 7,540,857 B2 | 6/2009 | Backman et al. | |
| 7,544,187 B2 | 6/2009 | Lampropoulos et al. | |
| 7,547,296 B2 | 6/2009 | Lampropoulos et al. | |
| 7,578,814 B2 | 8/2009 | Accisano, III et al. | |
| 7,582,105 B2 | 9/2009 | Kolster | |
| 7,591,805 B2 | 9/2009 | Lampropoulos | |
| 7,604,660 B2 | 10/2009 | Borg et al. | |
| 7,608,099 B2 | 10/2009 | Johnson et al. | |
| 2003/0028203 A1 | 2/2003 | Clark | |
| 2003/0195561 A1 | 10/2003 | Carley et al. | |
| 2004/0133239 A1 | 7/2004 | Singhatat | |
| 2004/0176798 A1 | 9/2004 | Epstein et al. | |
| 2004/0260344 A1 | 12/2004 | Lyons et al. | |
| 2005/0085855 A1 | 4/2005 | Forsberg | |
| 2006/0030886 A1 | 2/2006 | Clark | |
| 2006/0058844 A1 | 3/2006 | White et al. | |
| 2006/0069397 A1 | 3/2006 | Nobles et al. | |
| 2006/0106418 A1 | 5/2006 | Seibold et al. | |
| 2006/0106423 A1 | 5/2006 | Weisel et al. | |
| 2006/0190038 A1 | 8/2006 | Carley et al. | |
| 2006/0265006 A1 | 11/2006 | White et al. | |
| 2007/0004991 A1 | 1/2007 | Shelton | |
| 2007/0032820 A1 | 2/2007 | Chin-Chen et al. | |
| 2007/0032821 A1 | 2/2007 | Chin-Chen et al. | |
| 2007/0129755 A1 | 6/2007 | Abbott et al. | |
| 2007/0219467 A1 * | 9/2007 | Clark et al. | 600/585 |
| 2008/0015635 A1 | 1/2008 | Olsen et al. | |
| 2008/0015636 A1 | 1/2008 | Olsen et al. | |
| 2008/0097479 A1 | 4/2008 | Boehlke et al. | |
| 2008/0097484 A1 | 4/2008 | Lim et al. | |
| 2008/0208265 A1 | 8/2008 | Frazier et al. | |
| 2008/0243182 A1 | 10/2008 | Bates et al. | |
| 2008/0269785 A1 | 10/2008 | Lampropoulos et al. | |
| 2008/0300629 A1 | 12/2008 | Surti | |
| 2009/0005805 A1 | 1/2009 | Vries et al. | |
| 2009/0043246 A1 | 2/2009 | Dominguez | |
| 2009/0069847 A1 | 3/2009 | Hashiba et al. | |
| 2009/0076546 A1 | 3/2009 | Ashley et al. | |
| 2009/0143817 A1 | 6/2009 | Akerfeldt | |
| 2009/0234295 A1 | 9/2009 | Lampropoulos et al. | |

FOREIGN PATENT DOCUMENTS

| | | |
|---|---|---|
| WO | WO 2009/052509 A1 | 4/2009 |
| WO | WO 2009/114811 A2 | 9/2009 |

OTHER PUBLICATIONS

Clark, Twi et al., "Angiographic Changes Following the Use of a Purse-String Suture Hemostasis Device in Hemodialysis Access Interventions." *J Vasc Interv Radiol* 2009; 20:61-65.

Cohen, PR et al., "The purse-string suture revisited: a useful technique for the closure of cutaneous surgical wounds." Abstract, PubMed, U.S. National Library of Medicine National Institutes of Health; PMID: 17442069; *Int J Dermatol*. Apr. 2007; 46(4):341-247.

Hein AN et al., "Use of the Percutaneous Thrombolytic Device for the Treatment of Thrombosed Pseudoaneurysms during Mechanical Thrombectomy of Hemodialysis Grafts." *J Vasc Intery Radiol* 2001; 13:201-204.

Kwok PC, "Endovascular Treatment for Central Venous Stenosis due to Central Vein Catheterization for Hemodialysis." *Saudi J Kidney Dis Transpl* [serial online] 2004 [cited Nov. 18, 2009]; 15:338-345.

MacKay-Wiggan J et al., "Suturing Techniques." emedicine. medscape.com/article/1128240, updated May 1, 2009.

Shaw JA et al., "Use of suture-mediated vascular closure devices for the management of femoral vein access after transcatheter procedures." Abstract, PubMed, U.S. National Library of Medicine National Institutes of Health; PMID: 15558775; *Catheter Cardiovasc Interv.* Dec. 2004; 63(4):439-43.

Zaleski, GX et al., "Purse-String Sutures and Miniature Tourniquet to Achieve Immediate Hemostasis of Percutaneous Grafts and Fistulas: A Simple Trick with a Twist." *AJR*, vol. 175, pp. 1643-1645, Dec. 2000.

* cited by examiner

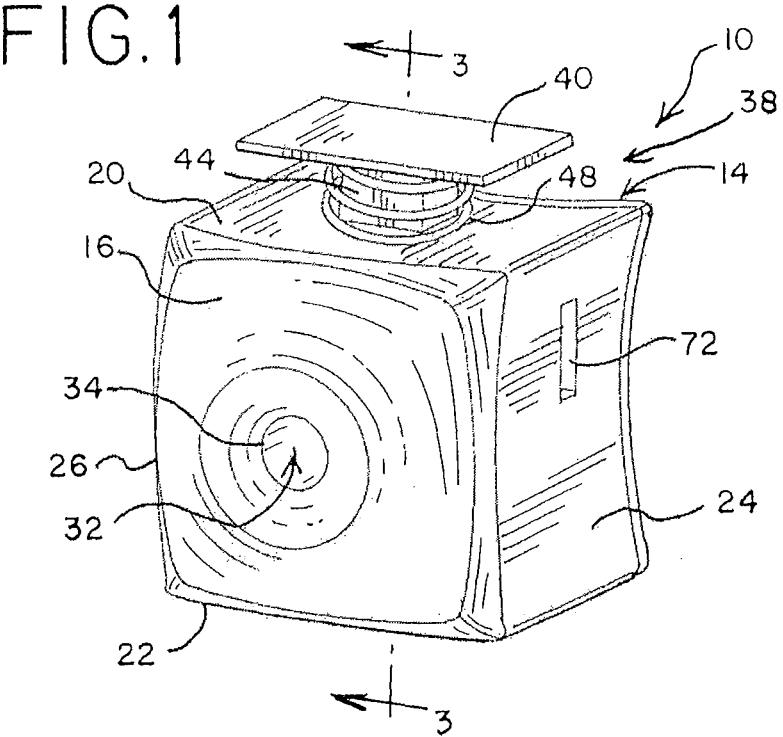
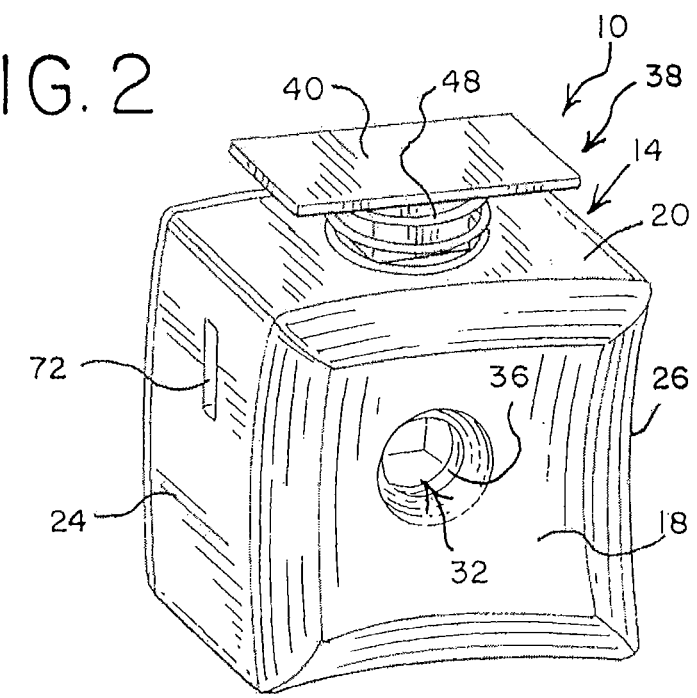

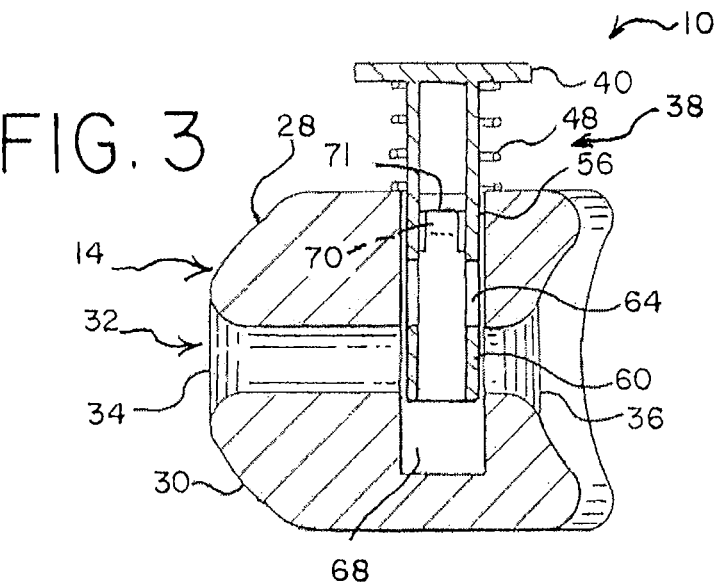
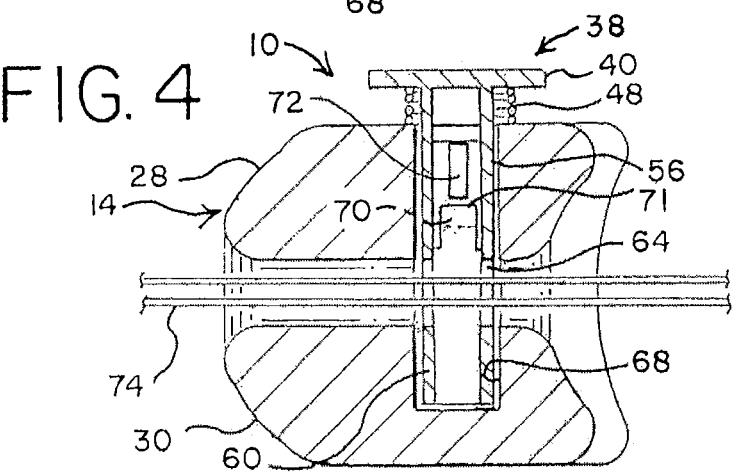
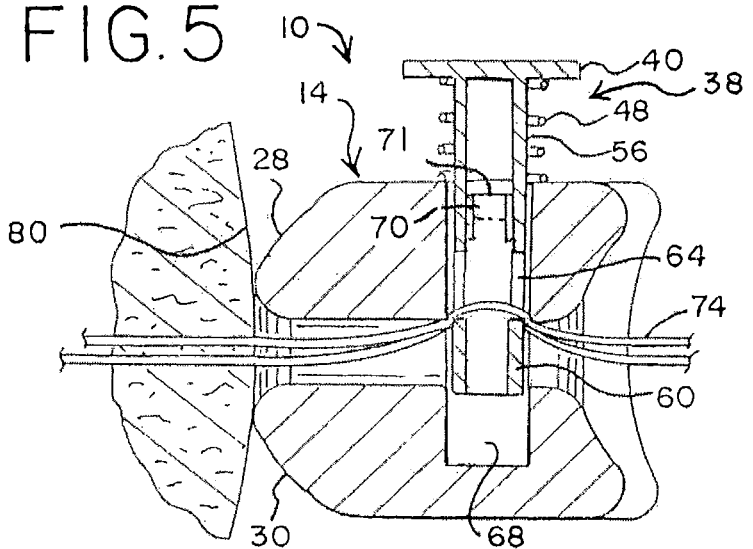

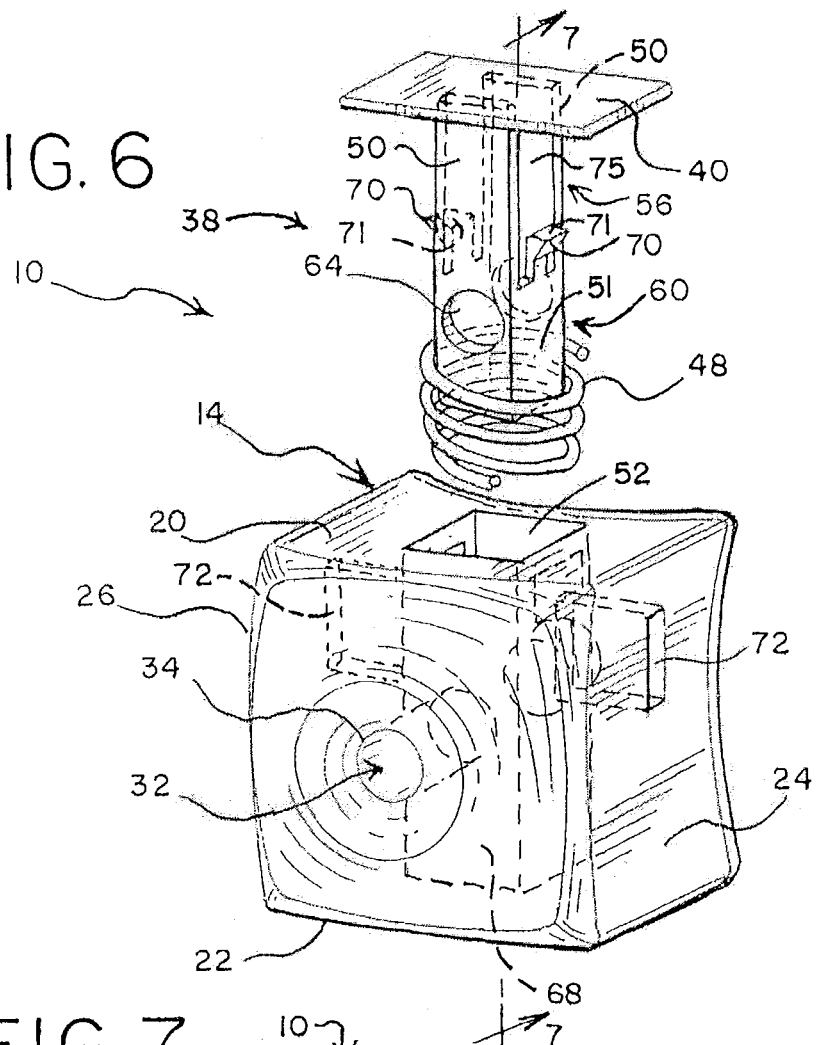
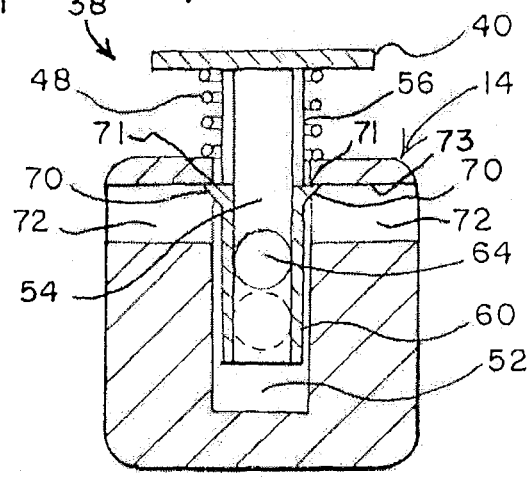

WOUND CLOSURE DEVICE

TECHNICAL FIELD

This invention relates generally to a wound closure device for promoting hemostasis in cutaneous wounds.

BACKGROUND

Percutaneous access of the vascular system for vascular device delivery is a common medical procedure. Typically this involves using a hollow needle to puncture the skin and a vessel, then introducing an introducer sheath to open the puncture site for the introduction of catheters and wire guides for navigation through the vascular system to facilitate delivery of suitable interventional devices. In many cases, vascular access requires introduction of catheters and wire guides through the femoral artery. Once the appropriate interventional procedure is completed, the introducer sheath is removed, sutures are applied to the puncture site and knotted to close the wound, and pressure is applied to the puncture site to stop the bleeding.

There are several disadvantages to the existing methodologies for treating cutaneous wounds. Achieving hemostasis with manual compression can be difficult, painful, and time-consuming. Moreover, removal of sutures may be difficult and painful, given their capacity to become buried within the tissues around the puncture site. In addition, in view of the close proximity of many cutaneous suture knots to high flow hemodialysis access sites, nurse practitioners may be reluctant to remove such sutures, thereby requiring additional attention by a doctor or secondary visits to the clinic or hospital. Although purse-string suture techniques are helpful for hemostasis, achieving precise tension on the sutures can be challenging.

In many cases, a purse-string suture technique is utilized to close wounds and promote hemostasis following hemodialysis treatment. Zaleski et al. discloses a modified purse-string suture technique involving placement of a miniature plastic dilator from a vascular sheath below a purse string suture to act as a "tourniquet", allowing tension on the purse-string suture to be adjusted by clockwise rotation of the tourniquet (Zaleski et al., AJR, Vol. 175, pp. 1643-1645, 2000). Following adjustment of the tension, the tourniquet is taped down and the sutures are left in place for a minimum of 24 hr., preferably 48-72 hours, before being removed, typically at the next dialysis session.

WO 2009/114811 A2 to Lampropoulos et al. discloses an elaborate suture securement system adapted for use with purse-string sutures. The system includes a suture securement apparatus 10 in conjunction with a threading assembly 20 (see, for example, FIG. 1). The suture securement apparatus includes a body employing a spring biased suture securing system that is connected to an extension tube for facilitating tensioning of the sutures at the suture insertion site. The threading assembly includes a suture loop functioning as a snare for pulling free suture tail ends into the suture securement apparatus. The elaborate system described by Lampropoulos includes many interacting components and does not appear to readily lend itself to hands-free use until hemostasis is achieved.

It would be advantageous and economical to eliminate unnecessary components or method steps in the design of a simple, easy to use, hands-free wound closure device. The present invention addresses the above-described problems and shortcomings, and provides a simple, easily manufactured device that can be easily deployed without leaving behind sutures or requiring the need for additional visits.

SUMMARY

In one aspect, a wound closure device for promoting hemostasis includes a polyhedral body comprising a proximal body end portion and a distal body end portion, including a suture channel extending between the proximal and distal body end portions, dividing the body into a first body portion and a second body portion, the suture channel containing proximal and distal suture channel openings. An actuator system includes a suture engagement member, the engagement member being configured to selectively facilitate axial movement or release of one or more sutures through the channel in an open configuration, and to facilitate securement of suture(s) in the channel in a locked configuration. The proximal body end portion includes a face configured to contact a body surface, anchoring the body to the body surface when suture(s) are secured under tension by the engagement member in the locked position.

In a preferred embodiment, the actuator system includes a spring activated biasing system, including a plunger slidably displaceable through a longitudinal channel extending through the first body portion. The plunger may be connectively linked to a button lever extending from the first body portion, the plunger being engaged by a spring biasing the plunger to render the suture channel open or closed.

In another embodiment, the present invention provides a method for promoting hemostasis using a wound closure device in accordance with the present invention. The method includes providing a wound closure device; grasping one or more sutures extending from a wound in a body surface; extending the distal end(s) of one or more sutures through the proximal and distal suture channel openings of the wound closure device while keeping the actuator depressed; holding the distal suture end(s) beyond the distal end portion of the wound closure device while keeping the actuator depressed; positioning the proximal body end portion against the wound; and releasing the actuator so that one or more portions of the suture(s) are secured in the suture channel, and so that the body of the device is anchored against the body surface surrounding the wound.

Depending on the extent to which the body of the device is compressed against the body surface surrounding wound while pulling the sutures away from the device in a distal direction, a desired level of hands-free tension can be obtained following release of the actuator. After anchoring the device to the body surface for sufficient period of time to achieve hemostasis, the device and the sutures may be removed.

BRIEF DESCRIPTION OF THE DRAWINGS

FIG. 1 is a front perspective view of a device according to one embodiment of the present invention.

FIG. 2 is a rear perspective view of the device in FIG. 1.

FIG. 3 is a cross-sectional view of the device in FIGS. 1 and 2, illustrating a resting or locked configuration precluding passage of sutures through the suture channel.

FIG. 4 is a cross-sectional view of the device in FIGS. 1 and 2, illustrating actuation of the plunger to create an open configuration allowing passage of sutures through the suture channel.

FIG. 5 is a cross-sectional view of the device in FIGS. 1 and 2, illustrating a release of the plunger, thereby securing the sutures to the suture channel in the locked configuration.

FIG. 6 is an exploded perspective of the device in FIGS. 1 and 2

FIG. 7 is a cross sectional view of the device in FIG. 6.

DETAILED DESCRIPTION

FIG. 1 depicts a cutaneous wound closure device 10 according to one embodiment of the present invention. The device 10 includes a polyhedral or spherical body 14. In FIG. 1, the body is depicted as a cuboidal body having a proximal end portion or front face 16, a distal end portion or rear face 18, a top face 20, a bottom face 22, a first side face 24, and a second side face 26. In FIG. 1, the front face 16 is convex-shaped and the rear face 18 is concave-shaped.

The body 14 may utilize any one of a variety of three-dimensional polyhedral or spherical shapes. A polyhedral body may contain a plurality of faces, including at least one wound-contacting face, any one of which may be flat, convex or concave in shape. Alternatively, the body 14 may utilize a "faceless" spherical, ellipsoid, oblate spheroid or prolate spheroid body or a hemispherical or catenoid shape having a single flat, convex or concave face opposite a single spherical, ellipsoid, oblate spheroid or prolate spheroid-shaped end body.

The body 14 may be made of ABS or polypropylene, or other material that can be conveniently and economically injection molded in large quantities. Alternatively, the body may be made of stainless steel, or other material that can be sterilized for re-use. The body 14 may be sized in accordance with the size and nature of the wound. In one embodiment, the body 14 may have a substantially cuboidal shape with convex, concave or substantially flat face. Each of the faces may have a length and width between about 5 mm to about 50 mm, preferably from about 10 mm to about 20 mm.

A hollow, substantially circular suture channel 32 is depicted as extending between proximal and distal end portions or faces, 16, 18, dividing the body 14 into a first body portion 28 and a second body portion 30. The suture channel 32 includes a proximal suture channel opening 34 and a distal suture channel opening 36. The suture channel 32 is configured to receive and allow passage of free suture end(s) therethrough, or securing the suture(s) at one or more locations, as discussed below.

The device 10 includes an actuator system 38, including a suture engagement member 44, which is configured to selectively facilitate axial movement or release of one or more suture(s) 74 through the suture channel 32 in an open configuration, and to facilitate securement of the suture(s) 74 in the channel 32 in a locked configuration. In one embodiment, as shown in FIGS. 1-7, the actuator system 38 is configured so that the open configuration constitutes an activated state and the locked configuration constitutes a non-activated or resting state. In another embodiment, the open configuration constitutes the actuator system 38 (not shown) is configured so that the open configuration constitutes a non-activated or resting state and the locked configuration constitutes an activated state.

In a preferred embodiment depicted in FIGS. 1-7, the actuator system 38 includes a spring-activated system comprised of a button lever 40 connectively linked to a spring-activated engagement member or plunger 44 extending though a substantially hollow longitudinal channel 52. The longitudinal channel 52 extends through the first body portion 28, the suture channel 32, and a distal channel portion or well 68 in the second body portion 30.

More particularly, FIGS. 3-5 depict a cross-sectional view of the device in FIGS. 1 and 2. FIG. 3 illustrates a resting or locked configuration precluding passage of sutures through the suture channel. FIG. 4 illustrates depression of the plunger to create an open configuration allowing passage of sutures through the suture channel. FIG. 5 illustrates release of the depressed plunger, producing a locked configuration in which the sutures are secured. FIG. 6 is an exploded perspective view of the device in FIGS. 1 and 2 showing additional features associated with the depicted actuator system. FIG. 7 is a cross sectional view of the device in FIG. 6.

FIGS. 3-7 depict an engagement member in the form of a plunger 44 having a substantially hollow structure, including oppositely positioned vertical faces 50 connected to the button lever 40. The plunger 44 includes a plunger opening 64 between a top plunger portion 56 and a bottom plunger portion, the plunger opening 64 extending through opposite plunger faces 50. In a resting position, a resilient biasing member, depicted as a spring 48, biases the bottom plunger portion 60 to block the suture channel 32 so as to create a closed or locked configuration in which axial movement of sutures 74 between the proximal and distal suture channel openings 34, 36 is blocked (FIG. 3).

Keyway channels 72 extend through the first body portion 28 from opposite body side faces 24, 26 (FIGS. 6 and 7). A pair of cantilevered locking teeth 70 extend from opposite plunger faces 51 extending from the bottom plunger portion 60, below an open plunger area 75. Each locking tooth 70 includes a tooth face 71 laying flush up against a top side 73 of the keyway channel 72 in the locked configuration so as to retain the plunger 44 in the longitudinal channel 52 and prevent release of the plunger 44 from the body 14 (FIGS. 6 and 7). Depression of the locking teeth 70 into a hollow portion 54 of the plunger 44 can facilitate insertion or removal of the plunger 44 from the body 14 via the longitudinal channel 52.

The plunger 44 includes a plunger opening 64 between the top plunger portion 56 and the bottom plunger portion 60, which is defined by a pair of apertures extending through opposite faces of the plunger 44 (FIGS. 6 and 7). The bottom plunger portion 60 is configured to move into the distal channel portion 68 following depression of the button lever 40 (FIG. 4). When the bottom plunger portion 60 moves into the distal channel portion 68, the plunger opening 64 aligns with the suture channel 32, creating a free path for axial movement of sutures 74 between the proximal and distal suture channel openings 34, 36 (FIG. 4). After the sutures 74 are passed through the suture channel 32, release of the button lever 40 to its resting state causes the bottom plunger portion 60 to spring upward so that vertical plunger faces 50 in the bottom plunger portion 60 block the suture channel such that the adjoining plunger face edges fixedly cinch the sutures to the suture channel 32 in a closed configuration (FIG. 5). Those of skill in the art will appreciate that the plunger 44 may be configured as a substantially hollow rod or as a substantially solid rod or rectangle having locking indentations and openings in the plunger 44 configured for engagement with complementary portions in the body 14 so as to create open or locked suture channel 32 configurations.

The actuator system 38 depicted in FIGS. 1-7 is connectively linked to the first body portion 28, although it may be linked to other sides or faces of the body 14, depending on the orientation of the device relative to the sutures 74 extending from the cutaneous surface 80. In FIGS. 1-7, the suture channel 32 is generally parallel to the top 20 and bottom 22 faces and perpendicular to the longitudinal channel 52. The proximal and distal end portions or faces 16, 18 are shaped to contact a wound (not shown) in an atraumatic fashion, anchoring the device 10 to a body surface 80 when suture(s) 74 are secured under tension by the engagement member 44 in a locked position. Those of skill in the art will appreciate that the body 14 may accommodate a variety of different faces or curved surfaces in the proximal end portion 16 so as to anchor the device 10 to a body surface 80 following securement of the suture(s) 74 thereto. Similarly, the angle of the suture channel 32 relative to the body 14 and relative to the longitudinal channel 52 may be modified depending on the nature of the suture(s) 74 and the need for directing an appropriate tensioning force thereto.

In another aspect, a method for promoting hemostasis includes grasping one or more suture(s) 74 extending from a wound, and extending (and locking) the suture(s) 74 into the suture channel 32 of any one of the above described wound closure devices 10.

More particularly, the suture(s) 74 are extended through the proximal suture channel opening 34 and the lumen of the suture channel 32 until the suture(s) 74 extend beyond the distal suture channel opening 36. Then, while holding one or more suture(s) 74 beyond the distal end portion or face 18, the proximal end portion or face 16 of the body 14 is positioned against a wound (not shown) in a cutaneous surface 80, for example. When a desired level of tension is obtained, the actuator system 38 is actuated so that one or more portions of the one or more sutures 74 are secured in suture channel 32 by the bottom plunger portion 60, and so that the body 14 of the device 10 is anchored against the wound and the sutures remain under tension (FIG. 5).

The present invention provides a method for promoting hemostasis in cutaneous wounds closed by a variety of different suturing techniques known to those of skill in the art. Accordingly, the cutaneous wound closure device 10 of the present invention can be applied to a variety of sutures, including but not limited to, running sutures, locked sutures, purse-string sutures, vertical mattress sutures, half-buried vertical mattress sutures, horizontal mattress sutures, and the like. Preferably, the sutures are not knotted before insertion through the wound closure device 10 and are in a configuration allowing rapid removal following use of the device 10. In some embodiments, anchoring the device 10 to the area of the wound with the sutures under tension precludes the need for a practitioner to hold the device 10 while waiting for hemostasis to be achieved. Once bleeding is stopped, the device 10 and the sutures 74 may be removed, in many cases within 20-60 minutes from the time that the device 10 is anchored to the wound.

The invention claimed is:

1. A cutaneous wound closure device comprising:
a cuboidal body comprising a convexly curved proximal body end portion and a generally complementary, concavely curved distal body end portion and two pairs of two opposed lateral surfaces extending from the proximal body end to the distal body end, the proximal body end and the distal body end having a distance from each other that is about equal to the distance between the two opposed lateral surfaces of each of the two pairs, the body comprising a suture channel horizontally extending through the proximal and distal body end portions and dividing the body into a first body portion and second body portion, the suture channel comprising proximal and distal suture channel openings;
an actuator system comprising a suture engagement member, the engagement member being configured to selectively facilitate axial movement or release of one or more sutures through the channel in an open configuration, and to facilitate securement of the suture(s) in the channel in a locked configuration,
wherein the actuator system comprises a spring-activated biasing system comprising a plunger slidably displaceable through a longitudinal channel extending between the proximal body portion and the distal body portion, the plunger having a bottom plunger portion arranged in the longitudinal channel and a top plunger portion extending partially outside the longitudinal channel, wherein the actuator system further comprises an abutment surface formed on the top plunger portion outside the body, and a compression spring extending between the body and the abutment surface, the compression spring having a first end and a second end, the first end abutting an outside surface of the body and the second end abutting the abutment surface,
wherein the proximal body end portion comprises a face configured to contact a body surface, anchoring the body to the body surface when suture(s) are secured under tension by the engagement member in the locked position;
wherein the proximal body end portion is free from structure protruding proximally therefrom, and the distal body end portion is free from structure protruding distally therefrom.

2. The device of claim 1, wherein the face has a length and a width between about 10 mm to 30 mm, and the proximal end portion is configured to contact a cutaneous surface.

3. The device of claim 1, wherein the actuator system is configured so that the open configuration constitutes an activated state and the locked configuration constitutes a non-activated state.

4. The device of claim 1, wherein the actuator system is configured so that the open configuration constitutes a non-activated state and the locked configuration constitutes an activated state.

5. The device of claim 1, wherein the spring biases the plunger to render the suture channel open or closed.

6. The device of claim 1, wherein the plunger comprises a substantially hollow rectangular structure and is connected to a button lever,
wherein a plunger opening extends through two oppositely spaced vertical plunger faces, the plunger opening disposed between the top plunger portion and the bottom plunger portion, and
wherein the biasing system is configured so that depression of the button lever causes the bottom plunger portion to become displaced into the longitudinal channel disposed in the second body portion, thereby aligning the plunger opening with the suture channel so as to create an open suture channel for passing one or more sutures therethrough.

7. The device of claim 1, wherein the top plunger portion includes locking teeth extending from opposite vertical plunger faces, each locking tooth comprising a locking tooth face engaged by a top surface of an open keyway extending from a body face in the locked configuration, wherein depression of the locking teeth into a hollow plunger area facilitates insertion or removal of the plunger through the longitudinal channel.

8. The device of claim 1, wherein the spring is a cylindrical coil spring surrounding the top plunger portion.

* * * * *